United States Patent
Li et al.

(10) Patent No.: US 7,645,447 B2
(45) Date of Patent: Jan. 12, 2010

(54) TREATING RETINAL DEGENERATION CAUSED BY RETINAL VEIN OCCLUSION OR RETINAL ISCHEMIA

(75) Inventors: Hung Li, Taipei (TW); Yih-Jing Lee, Taipei (TW)

(73) Assignee: Academia Sinica, Taipei (TW)

( * ) Notice: Subject to any disclaimer, the term of this patent is extended or adjusted under 35 U.S.C. 154(b) by 239 days.

(21) Appl. No.: 11/113,821

(22) Filed: Apr. 25, 2005

(65) Prior Publication Data

US 2006/0239964 A1  Oct. 26, 2006

(51) Int. Cl.
*A61K 38/18* (2006.01)
*A61K 35/14* (2006.01)
*A61K 35/28* (2006.01)
*C12N 5/08* (2006.01)

(52) U.S. Cl. ............... 424/93.7; 435/372; 514/4

(58) Field of Classification Search ............... None
See application file for complete search history.

(56) References Cited

U.S. PATENT DOCUMENTS 5,612,211 A * 3/1997 Wilson et al. ............ 435/378

FOREIGN PATENT DOCUMENTS

WO  2005/049062  * 6/2005

OTHER PUBLICATIONS

Merck Manual Online Medical Library, Retinitis Pigmentosa, Feb. 2003.*
Merck Manual Online Medical Library, Age-Related Macular Degeneration, Feb. 2003.*
Gough 1997. Lancet 350:855-859 .*
McFarland 2004. Expert Opin. Biol. Ther. 4:1053-1058.*
Huang 2004. IOVS 45 (Suppl. 2):U103; Annual Meeting of Association for Research in Vision and Ophthamology, Apr. 24-29, 2004; available online Feb. 23, 2004.*
Grant 2002. Nature Medicine 8:607-612.*
Wu Feb. 10, 2004, Molecular Vision 10:93-102.*
Kanda et al. "Electrophysiological Studies of the Feasibility of Suprachoroidal-Transretinal Stimulation for Artificial Vision in Normal and RCS Rats". Investigative Ophthalmology & Visual Science 45(2):560-566, Feb. 2004.
Rosenbaum et al. "Functional and Morphologic Comparison of Two Methods to Produce Transient Retinal Ischemia in the Rat" . . . Journal of Neuro Ophthalmology 21(1):62-68, 2001.
Miyahara et al., "Argatroban Attenuates Leukocyte- and Platelet-Endothelial Cell Interactions After Transient Retinal Ischemia," *Stroke*, 34:2043-2049 (2003).
Tsujikawa et al., "In Vivo Evaluation of Leukocyte Dynamics in Retinal Ischemia Reperfusion Injury," *Invest. Opthalmol. Vis. Sci.*, 39:793-800 (1998).
Tsujikawa et al., "Tacrolimus (FK506) Attenuates Leukocyte Accumulation After Transient Retinal Ischemia," *Stroke*, 29:1431-1438 (1998).

* cited by examiner

*Primary Examiner*—Daniel E. Kolker
(74) *Attorney, Agent, or Firm*—Occhiuti Rohlicek & Tsao LLP

(57) ABSTRACT

Methods of treating a retinal degenerative disorder.

20 Claims, No Drawings

TREATING RETINAL DEGENERATION CAUSED BY RETINAL VEIN OCCLUSION OR RETINAL ISCHEMIA

BACKGROUND

Retinal degeneration, a process of progressive and eventual death of retina cells, is a leading cause of vision loss and blindness. It results from various disorders or injuries (e.g., retinal ischemia and retinal neovascularization). As no reliable therapy is currently available, there is a need for an effective method of treating retinal degeneration.

SUMMARY

This invention is based, at least in part, on the discovery that retinal degeneration can be reversed by administration of granulocyte-colony stimulating factor (G-CSF) and, optionally, peripheral blood hematopoietic stem cells (PBSCs).

Accordingly, one aspect of this invention features a method of treating a retinal degenerative disorder, i.e., a disorder caused by loss, damage, or death of retinal cells (e.g., one caused by a retina ischemia). The method includes identifying a subject suffering from or being at risk for developing a retinal degenerative disorder, and administering to the subject an effective amount of G-CSF. The G-CSF can be administered subcutaneously 10 to 500 µg/day/kg body weight for 2-10 days (preferably, 20 to 200 µg/day/kg body weight for 3-8 day; and, more preferably 50-150 µg/day/kg body weight for 4-6 days). The PBSC can be administered each time at $1\times10^4$ to $1\times10^6$ cells (preferably $5\times10^4$ to $8\times10^6$; and more preferably $1\times10^5$ to $6\times10^5$ cells).

The above-described method can also include measuring the ability of the retina of the subject of sensing light before or after the administering step to confirm retina regeneration. The method can further include administering to the subject an effective amount of PBSCs. Preferably, the PBSCs are autologous to the subject. For example, the cells are enriched from the subject after the subject is administered G-CSF.

"Treating" refers to administration of a compound or composition (e.g., a cell composition) to a subject, who is suffering from or is at risk for developing retinal degeneration or a disorder causing retinal degeneration, with the purpose to cure, alleviate, relieve, remedy, or ameliorate the degeneration/disorder, the symptom of the degeneration/disorder, the disease state secondary to the degeneration/disorder, or the predisposition toward the degeneration/disorder. An "effective amount" refers to an amount of the compound or composition that is capable of producing a medically desirable result, e.g., as described above, in a treated subject. The treatment method can be performed alone or in conjunction with other drugs or therapies.

The details of one or more embodiments of the invention are set forth in the description below. Other features, objects, and advantages of the invention will be apparent from the description and the claims.

DETAILED DESCRIPTION

The present invention relates to using G-CSF, which mobilizes blood hematopoietic stem cells from bone marrow to peripheral blood, and to retinal for treating retinal degeneration. Like embryonic stem cells (ES cells), PBSCs possess potential to differentiate into various types of cells, including neuronal cells or glial cells, two major cell types in retina. PBSCs, as well as ES cells, therefore can be used to regenerate the neuronal or glial cells and thereby treat retinal degeneration. Indeed, studies have indicated that stem cell transplantation repair neural damage (Li et al., 2001, Cell Transplant. 10:31-40; and Chen et al. 2001, Stroke 32:2682-2688).

Ethical and logistical considerations have hampered the use of ES cells (Baringa, 2000, Science, 287(5457):1421-1422; and Boer, 1994, J. Neurol., 242(1):1-13). Due to fewer restrictions, PBSCs represent a promising alternative to other pluripotent cells. Nonetheless, the number of PBSCs under a steady-state condition is very low. Also conventional stem cell transplantation requires surgical intervention and is associated with a high cell mortality rate.

Within the scope of this invention is a method of treating retinal degeneration in a subject. The method includes identifying a subject suffering from or being at risk for developing retinal degeneration. The subject can be a human or a non-human mammal, such as a cat, a dog, or a horse. The retinal degeneration can be caused by retinal ischemia or neovascularization associated with retinal arterial occlusion or retinal vein occlusion. While retinal arterial occlusion and retinal vein occlusion are similar in pathogenesis, their clinical natures are different. Each of them has unique etiology, diagnosis, management, and prognosis. Retinal arterial occlusion is caused by a blockage of the arteries which reduces the blood supply to the retina. Retinal vein occlusion occurs when the circulation of a retinal vein becomes obstructed by an adjacent blood vessel. This obstruction results in stoppage of blood flow and hemorrhages in the retina.

A subject to be treated can be identified by standard diagnosing techniques for the conditions or disorders. The method of this invention entails administering to the subject an effective amount of a G-CSF.

While any type of G-CSF can be used, highly purified G-CSF is preferred. Examples of G-CSF include mammalian G-CSF (e.g., human G-CSF) or G-CSF having substantially the same biological activity as mammalian G-CSF. Both naturally occurring G-CSF and genetic engineered G-CSF can be used. G-CSF obtained by recombinant DNA technology may be that having the same amino acid sequence as naturally occurring G-CSF or an functionally equivalent thereof. A "functional equivalent" refers to a polypeptide derivative of a naturally occurring G-CSF, e.g., a protein having one or more point mutations, insertions, deletions, truncations, a fusion protein, or a combination thereof. It posses the activity of G-CSF, i.e., the ability to mobilize stem cells from bone marrow into peripheral blood. For reports on G-CSF derivatives, see U.S. Pat. Nos. 5,581,476; 5,214,132; 5,362,853; and 4,904,584. The term "G-CSF" also covers chemically modified G-CSF. Examples of chemically modified G-CSF include G-CSF subjected to conformational change, addition or deletion of the sugar chain, and G-CSF to which a compound such as polyethylene glycol has been bound (see, e.g., U.S. Pat. Nos. 5,824,778, and 5,824,784; WO 96/11953, WO 95/21629, WO 94/20069, U.S. Pat. No. 5,218,092, JP 1992-164098 A). Once purified and tested by standard methods, G-CSF can be administered to a subject for mobilizing and enriching PBSCs as described above. G-CSF is administered at, e.g., 10 to 500 µg/day/kg body weight for 2-10 days. The G-CSF can be administered to a subject via any suitable routes. Examples include subcutaneous, intramuscular, or intraperitoneal injection.

The method of this invention optionally includes administering to a subject an effective amount of PBSCs. Both heterologous and autologous PBSC can be used. In the former case, HLA-matching should be conducted to avoid or minimize host reactions. In the latter case, autologous PBSCs are enriched and purified from a subject to be treated before the cells are introduced back to the subject. In both cases, G-CSF is used as the active ingredient to mobilize stem cells from bone marrow into peripheral blood so as to facilitate enriching and purifying the PBSCs and homing to the retina. In a preferred embodiment, PBSCs are obtained from a subject as follows. First, the subject is administered G-CSF to mobilize hematopoietic stem cells (HSCs) from bone marrow into the peripheral blood. After this enriching step, PBSCs are purified from the peripheral blood.

PBSCs can be purified based on their physical and biochemical properties. For example, peripheral blood cells may be concentrated for hematopoietic stem cells by centrifugation, counter-current elutriation, selection with cell surface markers (e.g., CD34+ or stem cell related antibodies), or removal of lineage positive (committed) hematopoietic cells. Such methods are well-known in the art. See e.g., U.S. Pat. Nos. 5,061,620; 5,087,570; 5,061,620; 4,714,680; 4,965,204; and 5,035,994.

Purified PBSCs are tested and stored by standard techniques. They can be administered to a subject in need thereof. In general, $1\times10^4$ and $1\times10^6$ (e.g., $5\times10^4$ to $8\times10^6$ and more preferably $1\times10^5$ to $6\times10^5$) cells are administered each time. Multiple sites can be used depending on the location and nature of particular damage. Coordinates of the sites can be determined accordingly based on comparative anatomy.

Before or after the above-described administration, a subject can be examined to confirm treatment efficacy. To this end, one can use various standard tests or techniques, such as electroretinogram, direct and indirect ophthalmoscopy, visual acuity, refraction test, color defectiveness determination, pupillary reflex response, slit lamp examination, intraocular pressure determination, ultrasound of the eye, retinal photography, and fluorescein angiography. Preferred is electroretinogram, which records the electrical currents in the retina produced by visual stimuli. See, e.g., Rosenbaum et al., J. Neuroophthalmol. 2001 March; 21(1):62-8 and Kanda et al., Invest. Ophthalmol Vis. Sci. 2004 February; 45(2):560-6.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Rat retinal ligation and reperfusion models of retinal ischemia were used to examine the effects of G-CSF on retinal damage caused by retinal ischemia or retinal vessel occlusion.

Male SD rats (150-250 g) were maintained in a 12 hour-light/12 hour-dark pathogen-controlled environment and were allowed access to food and drink ad libitum. The rats were housed in the Animal Care Facility at the Fu-Jen Catholic University under standard animal care guidelines. All protocols were in accordance with ARVO's (the Association for Research in Vision and Ophthalmology) Statement for the Use of Animals in Ophthalmic and Vision Research and approved by the animal care and use committee of Academia Sinica.

Transient optic ischemia was induced according to a method modified from those described in Faberowski et al. and Rosenbaum et al. (Invest Ophthalmol. Vis. Sci. 1989, 30:2309-2313; and J. Neuroophthalmol., 2001, 21:62-68.).

More specifically, the above-mentioned rats were anesthetized with sodium pentobarbital (40 mg/kg; Sigma, St. Louis, Mo., USA). Both pupil of each rat were dilated with 1% tropicamide (Alcon, Puurs, Belgium). After a lateral conjunctival peritomy and disinsertion of the lateral rectus muscle, the optic sheath of the right eye was exposed, and a sterile 2-0 nylon suture was passed around the optic sheath and tightened until blood flow ceased in all retinal vessels. The absence of blood perfusion was confirmed by a dissection microscope. The suture was removed 90 minutes later. The left eye of each rat was subjected to a sham operation and designated as the "contralateral control." The rats were maintained anesthetized by intraperitoneal injection of sodium pentobarbital if necessary and kept on a heating pad when recovering from anesthesia.

The rats were divided into three groups. The rats in Group 1 were subcutaneously administered G-CSF (100 µg/kg body weight; Chugai Pharmaceutical Co., Tokyo, Japan) once a day for five days after the ischemic operation. The rats in Group 2 (Control group) were administered saline in the same manner for five days. The rats in Group 3 remained untreated after the retinal ischemia. In addition, some rats in each of the three groups were injected intraperitoneally with BrdU (50 mg/kg,; Sigma, St. Louis, Mo., USA) daily for 14 days before sacrifice. A cumulative BrdU labeling was performed to examine the population of proliferating cells during the 14 days after the retinal ischemia.

Morphometric and quantitative analyses were then conducted. Both eyes of each of the above-described rat were collected 7 or 14 days after the retinal ischemia operation. The specimens were fixed in 4% paraformaldehyde-PBS (pH 7.4), washed with PBS, and cryostate-sectioned at 5 µm thickness. Some of the sections were stained with hematoxylin and eosin (H&E) for cell counts and morphological study.

It was found that the G-CSF-treated rats showed less ischemia-caused apoptosis in retinas. Each retina includes several cell layers: the ganglion cell layer, inner nuclear layer (INL), outer nuclear layer (ONL). The ganglion cells are distributed in the inner layer. The INL contains the nuclei of bipolar cells, amacrine cells, and horizontal cells. The ONL contains nuclei of photoreceptors. Histological morphology results showed that, 14 days after the operation, the retina subjected to ischemic operation had fewer cells in all three layers than the contralateral retina. It was found that the subretinal space of the ischemic retina was enlarged, indicating detachment of the retina. In contrast, the retina remained in a normal condition in the contralateral control eye. In the rats treated with G-CSF, more cells appeared in all three layers of the retina than in the rats not treated with G-CSF. The cells in the treated rats were found less apoptotic after administration of G-CSF. These results suggest that G-CSF prevented or repaired cell loss.

EXAMPLE 2

It is possible that G-CSF protects retina cells from ischemia-caused apoptosis, or induces the HSCs releasing from bone marrow and mobilizing to the injury area for cell renewal. To find out the possible mechanism, BrdU labeling was conducted.

More specifically, some of the above-mentioned sections were examined for BrdU immunoreactivity. The cryostate sections were fixed in 4% paraformaldehyde-PBS (pH 7.4) for 10 minutes and washed with PBS. A solution of 2×SSC (Sigma, St. Louis, Mo., USA) and 50% formamide (Amersham Biosciences, England) was applied to the sections and incubated for 2 hours at 65° C. The sections were then incubated for 30 minutes at 37° C. with 2N HCl (JT Baker, Phillipsburg, N.J., USA). After rinsed with PBS, the sections were preincubated with a blocking solution for 1 hour at room temperature and then incubated overnight at 4° C. with mouse monoclonal anti-BrdU antibody (sc-20045, Santa Cruz Biotechnology, California, USA). On the following day, the sections were stained with 3,3-diamino-benzidine (DAB) substrate and mounted for observation.

The result showed proliferating cells (BrdU+) in injured retina. G-CSF-treated rats had more BrdU labeled cells in the apoptotic retina area than the non-treated or saline-treated rats. BrdU labeled cells were found in both the subretinal space and the ganglion cell layers, suggesting that these cells might move to the injured area via the blood vessels in choroids (subretinal) and optic artery (inner retinal). The results indicate that G-CSF induced release of bone marrow HSCs so as to repair degenerating retinal cells after ischemia.

Epi-fluorescent immunohistochemistry was performed to examine retinal cells or differentiating cells in retina. Cryostate retina sections (5 μm) were prepared and fixed in 4% paraformaldehyde-PBS in the same manner described above. The sections were mounted on slides coated with poly-D-lysine and laminin (both from Sigma, St. Louis, Mo., USA). Primary antibodies against G-CSFR, CD34, STAT3, and phosphorylated STAT3 were obtained from Santa Cruz Biotechnology, California, USA). The slides were pre-warmed to room temperature, immersed in PBS, and placed in a moist chamber while incubating with the antibodies. The sections were incubated with primary antibodies that were diluted in 3% BSA-PBS for two hours at room temperature (for polyclonal antibody) or overnight at 4° C. (for monoclonal antibody). The slides were then incubated with secondary antibodies for 30 minutes at room temperature. After washing several times in PBS, the slides were mounted in an antifading mounting agent (DAKO Co., USA). For negative control, primary antibodies were replaced by non-immune IgG.

The result showed that no G-CSFR+ cells were found in controlateral retinas. G-CSFR+ cells were found in the injured retina area, indicating mobilization of bone marrow cells to the retinas. Also, more G-CSFR+ cells were found in the subretinal space in the G-CSF-treated rats than in saline-treated or non-treated rats, as well as the sham-operated rats. Also, CD34+ cells were found in the ischemic retinas. G-CSF treated rats had more CD34+ cells in the ischemic retinas than non- or saline-treated rats. As the G-CSFR+ cells were found also CD34+, they most likely to be hematopoietic progenitor cells.

The results indicate that G-CSF mobilized HSCs from bone marrow to the injured retina area post-ischemia cell repairing or renewing. This process might involve signal transducers and activators of transcription (STAT), a family of transcription factors that mediate the induction of cytokines and growth factors in various biological responses. STAT mediates apoptotic signals or cell repairing depending upon particular stimulus and cell types (Battle et al., 2002. Curr. Mol. Med. 2:381-392.). To elucidate the mechanism for retina repairing by G-CSF, STAT expressions and activities in retina were examined by immunohistochemistry.

It was found that G-CSF-treated rats had more phosphorylated STAT3+ (pSTAT3+) cells in the subretinal space of ischemic retinas than non- or saline-treated rats. Also, in each G-CSF-treated rat, the ischemic retina had more pSTAT3+ cells than the controlateral retina. The pSTAT3+ cells were distributed around the injured ischemic area. These results indicate that STAT3 mediated the cell protecting/repairing process in the injured retina.

Expression of markers for ganglion cells and rod cells, Thy1 and opsin, was examined to evaluate cell survival. Total mRNAs were prepared from ischemic retinas and contralateral control retinas of rats treated with or without G-CSF. A FastStart DNA Master SYBR Green kit (Roche, Germany) was used. Each amplification reaction was carried out in a total volume of 20 μl containing 2.5 mM $MgCl_2$, 0.5 μM each primer, 2 μl template DNA, and a master mix containing a reaction buffer, dNTPs, and taq DNA polymerase. The primers used were list below:

Thy1:

```
                                         (SEQ ID NO:1)
     Forward: TGCCTGGTGAACCAGAACCTT (SEQ ID NO:2)
     Reverse: TCACAGAGAAATGAAGTCCGTGGC
```

Opsin:

```
                                         (SEQ ID NO:3)
     Forward: GAGCAGCCGCAGTACTACCTG (SEQ ID NO:4)
     Reverse: AGCACAGGCCAACGCCATGA
```

GAPDH,

```
                                         (SEQ ID NO:5)
     Forward: CCCTTCATTGACCTCAACTA (SEQ ID NO:6)
     Reverse: CCAAAGTTGTCATGGATGAC
```

Each amplification was performed under the following conditions: a pre-incubation for 10 minutes at 95° C., followed by 45 cycles of 95° C. denaturation for 10 seconds/58° C. annealing for 10 seconds/72° C. extension for 15 seconds. Melting curve analysis was conducted for product identification. Data were analyzed by the LightCycler software (Roche, Germany) and the relative MRNA concentrations of the target gene in each sample were determined. Student's t-test and one-way ANOVA test with Bonferroni multiple comparison were used to compare significant differences between groups.

The result suggests that the expressions of both Thy1 and opsin were decreased in the ischemic retinas. However, the decreases were reversed by the treatment of G-CSF, indicating that G-CSF prevented retinal cell loss by, e.g., mobilizing HSCs to the injured retina area. The HSCs may differentiate into specific retinal cells or retinal progenitor cells for cell repair and regeneration.

Electroretinogram, a common method for evaluating retina function, was used to evaluate the visual function of the above-described rats. Both a-wave and b-wave of experimental eyes and contralateral eyes were recorded. It was found that the function of retina decayed 14 days after the retinal ischemic operation. More specifically, ischemic eyes had significant less a-wave and b-wave than contralateral eyes. In the rats treated with G-CSF, there was not much difference between the ischemic eye and the contralateral eye. The results indicate that G-CSF prevented or protected retinal cell from apoptosis after ischemia.

The above results suggest that G-CSF induced the release of HSCs from bone marrow to damaged retina areas. Damaged cells in the retina secreted trophic factors, which guided the HSCs to migrate to the retina and repair the injury retina.

HSCs have been shown to constitutively express interleukins (Majka, et al. 2001. Blood 97:3075-3085). These cytokines may be survival, growth, or differentiation factors for retinal neuronal progenitor cells which may proliferate, migrate, and differentiate following ischemia, thereby contributing to damage recovery processes.

It is known that stromal-cell derived factor 1 (SDF-1) may play an important role in mobilizing stem cells from bone marrow to the injured area in myocardial infarction (Askari et al. 2003, Lancet 362:697-703. 27). Apoptotic cells in the injured area may release SDF1 to attract HSC to the injured area for cell repairing or regeneration. This raises the possibility that HSCs may be directly involved in promoting plasticity of ischemically damaged neurons and endothelial cells. As described therein, more CD34+ cells were found in the ischemic retina than in the contralateral eye of the experimental animals, suggesting that ischemia-induced chemotactic factors, most likely to be SDF-1, might target HSCs to damaged tissues. Similarly, in a model of hepatic injury, regenerated hepatic cells were shown to be of bone marrow origin (Petersen et al., 1999, Science 284:1168-1170). Shyu et al. also found a similar effect in the brain of a stroke model (Shyu et al., 2004, Circulation 110:1847-1854). These findings suggest that injured cells might release chemokines to specifically attract HSCs proliferation and differentiation for cell regeneration in the damaged tissue.

STATs were found to be important in mediating the effects of numerous cytokines, polypeptide growth factors, hormones and oncoproteins (Bowman et al., 2000, Oncogene 19:2474-2488; and Horvath, 2000, Trends Biochem. Sci. 25:496-502.). A number of studies have defined both pro-apoptotic and anti-apoptotic signaling pathways mediated by STAT transcription factors (Battle et al., 2002, Curr. Mol. Med. 2:381-392. 15). In particular, STAT3 is believe to protect cells against apoptosis and mediate photoreceptor differentiation in the retina (Ozawa et al., 2004, Mol. Cell Neurosci. 26:258-270; and Zhang et al., 2004, Invest Ophthalmol. Vis. Sci. 45:2407-2412). Inhibition of STAT3 was found to induce apoptosis in multiple myeloma, melanoma, and other types of cancer (Battle et al., 2002, Curr. Mol. Med. 2:381-392. 15). In a glaucoma model, STAT3 was found to be involved in the process of retinal ganglion cell degeneration and repair (Thanos et al., 2004, Exp. Eye Res. 79:119-129. 34). Adamus et al. (J. Autoimmun. 21:121-129. 35) also shows that STAT3 plays an important role in photoreceptor protection from apoptotic death in a retinal degenerative model. In the experiment described above, it was found that STAT3 was activated or phosphorylated in the area of retinal cell repair. This suggests that STAT3 was involved in the cell regenerative process after the retinal ischemia. It was also found that there was more pSTAT3 in the G-CSF treated ischemic eye than in the non-treated ischemic eye, suggesting that cell regeneration or repair was promoted by G-CSF-pSTAT3 pathway.

Retinal occlusions may occur in various conditions, such as after acute retinal vascular occlusion, carotid artery disease, or other ocular disorders accompanied with systemic cardiovascular diseases (Ffythce, 1974, Trans Ophthal Soc UK 94:468-479). Ischemic retinal diseases may result in sight loss once severe retinal cell apoptosis occurs. There has been still no satisfied therapy to cure this retinopathy. Stem cell transplantation may be a potential method in this therapy. However, cell transplantation procedures are complex multi-step processes involving the isolation, in vitro expansion and differentiation of autologous stem cells from mesenchymal tissue, such as bone marrow. In addition, these treatment protocols require surgical intervention and the injection of foreign cells into patients, as well as the need for syngenic donors, as the sources of the transplanted cells. In addition, the donor stem cells have to be pre-cultured for differentiating into various of retinal cells or retina progenitor cells prior to the transplantation operated. Due to the complexity, success rates are not as good as expected. In contrast, the treatment strategies described in this invention could eliminate surgical procedures and obviate the use of foreign cells, hence reducing the risks of transmissible infectious agents and unwanted immune response. Thus, the G-CSF therapy has great advantage of a non-invasive therapy for retinal degenerative diseases caused by ischemia or vascular retinopathy.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating a retinal degenerative disorder caused by retinal ischemia or a retinal vein occlusion, comprising identifying a subject suffering from the retinal degenerative disorder, and
administering to the subject an effective amount of a granulocyte-colony stimulating factor and administering to the subject an effective amount of peripheral blood hematopoietic stem cells.

2. The method of claim 1, wherein the peripheral blood hematopoietic stem cells are autologous to the subject.

3. The method of claim 2, wherein the peripheral blood hematopoietic stem cells are obtained from the subject after the subject is administered the granulocyte-colony stimulating factor.

4. The method of claim 1, wherein the granulocyte-colony stimulating factor is administered subcutaneously.

5. The method of claim 1, wherein the granulocyte-colony stimulating factor is administered at 10 to 500 μg/day/kg body weight once a day for 2 to 10 days.

6. The method of claim 5, wherein the granulocyte-colony stimulating factor is administered at 20 to 200 μg/day/kg body weight once a day for 3 to 8 days.

7. The method of claim 6, wherein the granulocyte-colony stimulating factor is administered at 50-150 μg/day/kg body weight once a day for 4-6 days.

8. The method of claim 1, wherein the peripheral blood hematopoietic stem cells are administered at $1 \times 10^4$ to $1 \times 10^6$ cells.

9. The method of claim 1, wherein the peripheral blood hematopoietic stem cells are administered at $5 \times 10^4$ to $8 \times 10^6$ cells.

10. The method of claim 1, wherein the peripheral blood hematopoietic stem cells are administered at $1 \times 10^5$ to $6 \times 10^5$ cells.

11. The method of claim 1, further comprising measuring the ability of the retina of the subject to sense light after the administering step to confirm retina regeneration.

12. The method of claim 11, wherein the peripheral blood hematopoietic stem cells are autologous to the subject.

13. The method of claim 12, wherein the peripheral blood hematopoietic stem cells are obtained from the subject after the subject is administered the granulocyte-colony stimulating factor.

14. The method of claim 11, wherein the granulocyte-colony stimulating factor is administered subcutaneously.

15. The method of claim 11, wherein the granulocyte-colony stimulating factor is administered at 10 to 500 μg/day/kg body weight once a day for 2 to 10 days.

16. The method of claim 15, wherein the granulocyte-colony stimulating factor is administered at 20 to 200 μg/day/kg body weight once a day for 3 to 8 days.

17. The method of claim 16, wherein the granulocyte-colony stimulating factor is administered at 50-150 μg/day/kg body weight once a day for 4-6 days.

18. The method of claim 11, wherein the peripheral blood hematopoietic stem cells are administered at $1 \times 10^4$ to $1 \times 10^6$ cells.

19. The method of claim 11, wherein the peripheral blood hematopoietic stem cells are administered at $5 \times 10^4$ to $8 \times 10^6$ cells.

20. The method of claim 11, wherein the peripheral blood hematopoietic stem cells are administered at $1 \times 10^5$ to $6 \times 10^5$ cells.

* * * * *

UNITED STATES PATENT AND TRADEMARK OFFICE
CERTIFICATE OF CORRECTION

PATENT NO.       : 7,645,447 B2                                         Page 1 of 1
APPLICATION NO.  : 11/113821
DATED            : January 12, 2010
INVENTOR(S)      : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 273 days.

Signed and Sealed this

Twenty-first Day of December, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
tgcctggtga accagaacct t                                         21

<210> SEQ ID NO 2
<211> LENGTH: 24
<212> TYPE: DNA

-continued

```
<213> ORGANISM: Artificial Sequence
<220> FEATURE:
<223> OTHER INFORMATION: Primer

<400> SEQUENCE: 2
tcacagagaa atgaagtccg tggc                                            24

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gagcagccgc agtactacct g                                               21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agcacaggcc aacgccatga                                                 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cccttcattg acctcaacta                                                 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ccaaagttgt catggatgac                                                 20
```